United States Patent [19]
Walbrink et al.

[11] Patent Number: 5,449,356
[45] Date of Patent: Sep. 12, 1995

[54] MULTIFUNCTIONAL PROBE FOR MINIMALLY INVASIVE SURGERY

[75] Inventors: Harold J. Walbrink, Laguna Niguel, Calif.; Paul P. Burek, Aurora, Colo.; William J. Bowers; Donald L. Emmons, El Monte, both of Calif.

[73] Assignee: Birtcher Medical Systems, Inc., Irvine, Calif.

[21] Appl. No.: 779,101

[22] Filed: Oct. 18, 1991

[51] Int. Cl.⁶ ............................................. A61B 17/36
[52] U.S. Cl. ...................................... 606/49; 606/40; 606/37; 606/41
[58] Field of Search ............................. 606/49, 40–42, 606/45, 46, 37, 39, 29

[56] References Cited

U.S. PATENT DOCUMENTS

| | | |
|---|---|---|
| 1,731,627 | 10/1929 | Johnson et al. . |
| 1,952,617 | 3/1934 | Wappler . |
| 2,011,169 | 8/1935 | Wappler . |
| 2,022,065 | 11/1935 | Wappler . |
| 2,047,535 | 7/1936 | Wappler . |
| 2,688,329 | 3/1953 | Wallace . |
| 3,799,168 | 3/1974 | Peters ............................ 606/49 |
| 3,825,004 | 7/1974 | Durden, III . |
| 3,828,780 | 8/1974 | Morrison, Jr. . |
| 3,834,392 | 9/1974 | Lampman et al. . |
| 3,858,586 | 1/1975 | Lessen . |
| 3,902,494 | 9/1975 | Haberlen et al. . |
| 3,906,955 | 9/1975 | Roberts . |
| 4,016,881 | 4/1977 | Rioux et al. . |
| 4,040,426 | 8/1977 | Morrison, Jr. . |
| 4,057,064 | 11/1977 | Morrison, Jr. et al. . |
| 4,060,088 | 11/1977 | Morrison, Jr. et al. . |
| 4,245,624 | 1/1981 | Komiya . |
| 4,347,842 | 9/1982 | Beale . |
| 4,562,838 | 1/1986 | Walker . |
| 4,650,462 | 3/1987 | De Satnick et al. . |
| 4,706,655 | 11/1987 | Krauter . |
| 4,735,603 | 3/1988 | Goodson et al. . |
| 4,740,047 | 4/1988 | Abe et al. . |
| 4,760,840 | 4/1988 | Fournier, Jr. et al. . |
| 4,781,175 | 11/1988 | McGreery et al. . |
| 4,836,187 | 6/1989 | Iwakoshi et al. . |
| 4,878,893 | 11/1989 | Chin . |
| 4,882,777 | 11/1989 | Narula . |
| 4,901,719 | 2/1990 | Trenconsky et al. . |
| 4,901,720 | 2/1990 | Bertrand . |
| 4,919,129 | 4/1990 | Weber, Jr. et al. . |
| 4,920,980 | 5/1990 | Jackowski . |
| 4,943,290 | 7/1990 | Roxroth et al. ............... 606/49 |
| 4,949,706 | 8/1990 | Thon . |
| 4,998,527 | 3/1991 | Meyer . |
| 5,006,109 | 4/1991 | Douglas et al. . |
| 5,013,294 | 5/1991 | Baier . |
| 5,041,110 | 8/1991 | Fleenor . |
| 5,084,012 | 1/1992 | Kelman . |
| 5,088,997 | 2/1992 | Delahuerga et al. ......... 606/49 |
| 5,098,430 | 3/1992 | Fleenor ........................ 606/49 |
| 5,109,830 | 5/1992 | Cho . |
| 5,207,675 | 5/1993 | Canady ........................ 606/40 |
| 5,256,138 | 10/1993 | Burek et al. ................. 606/42 |
| 5,304,176 | 4/1994 | Phillips ....................... 606/40 |

*Primary Examiner*—Lee S. Cohen
*Assistant Examiner*—Brian L. Casler
*Attorney, Agent, or Firm*—John R. Ley

[57] ABSTRACT

A probe for use in minimally invasive surgery incorporates a nozzle and electrode assembly at the distal end of the probe for achieving gas assisted electro-fulguration. In addition, the probe accommodates the simultaneous use of other auxiliary surgical instruments, such as standard electrosurgical electrodes, laser fiber optic conduits and mechanical tools. Further still, the probe includes a passageway for achieving evacuation, irrigation or aspiration at the surgical site. The probe thus allows a surgeon to achieve multiple different surgical functions during a minimally invasive surgical procedure without removing one probe and inserting a different probe to achieve a different surgical function.

38 Claims, 3 Drawing Sheets

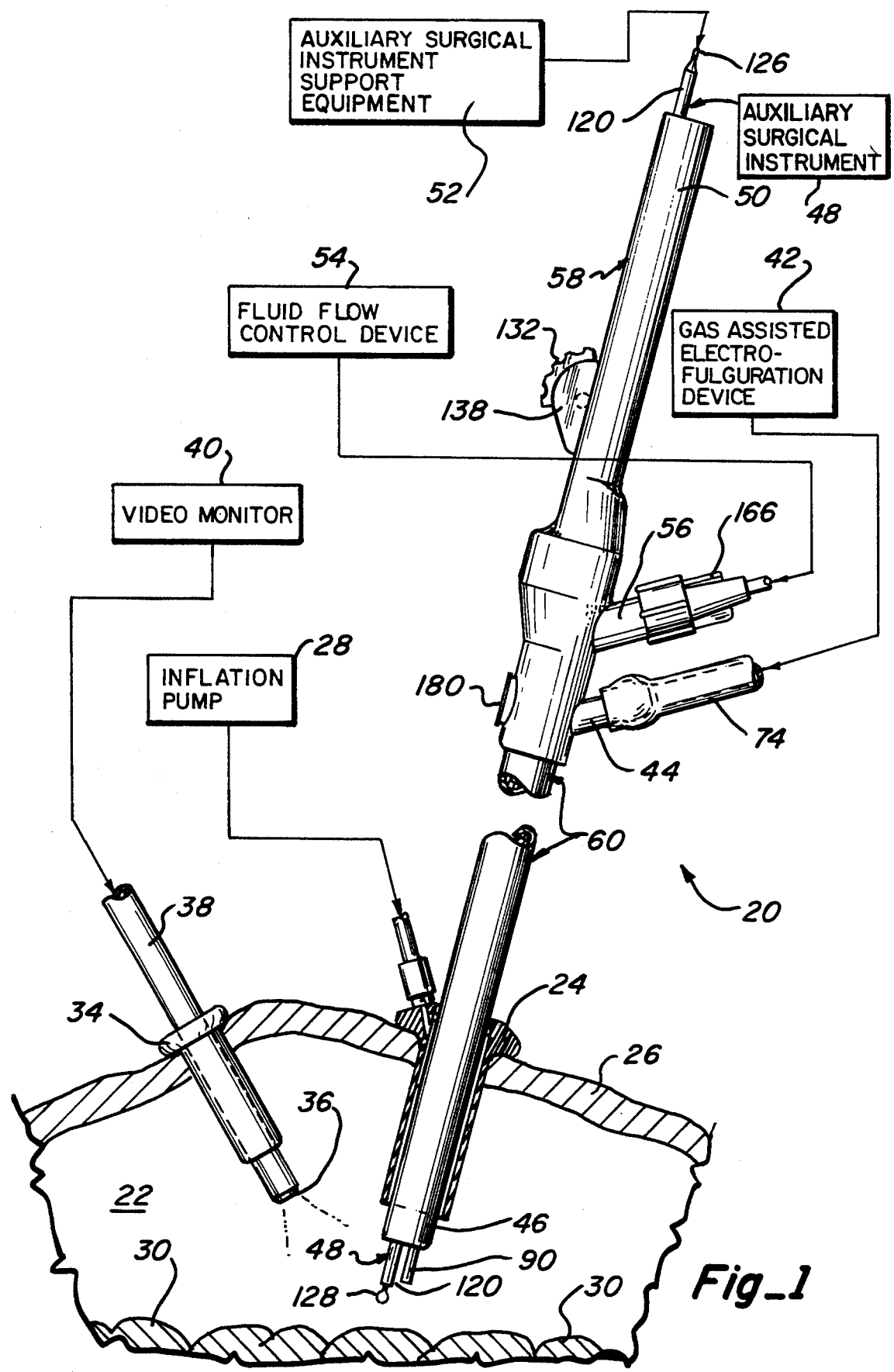
Fig_1

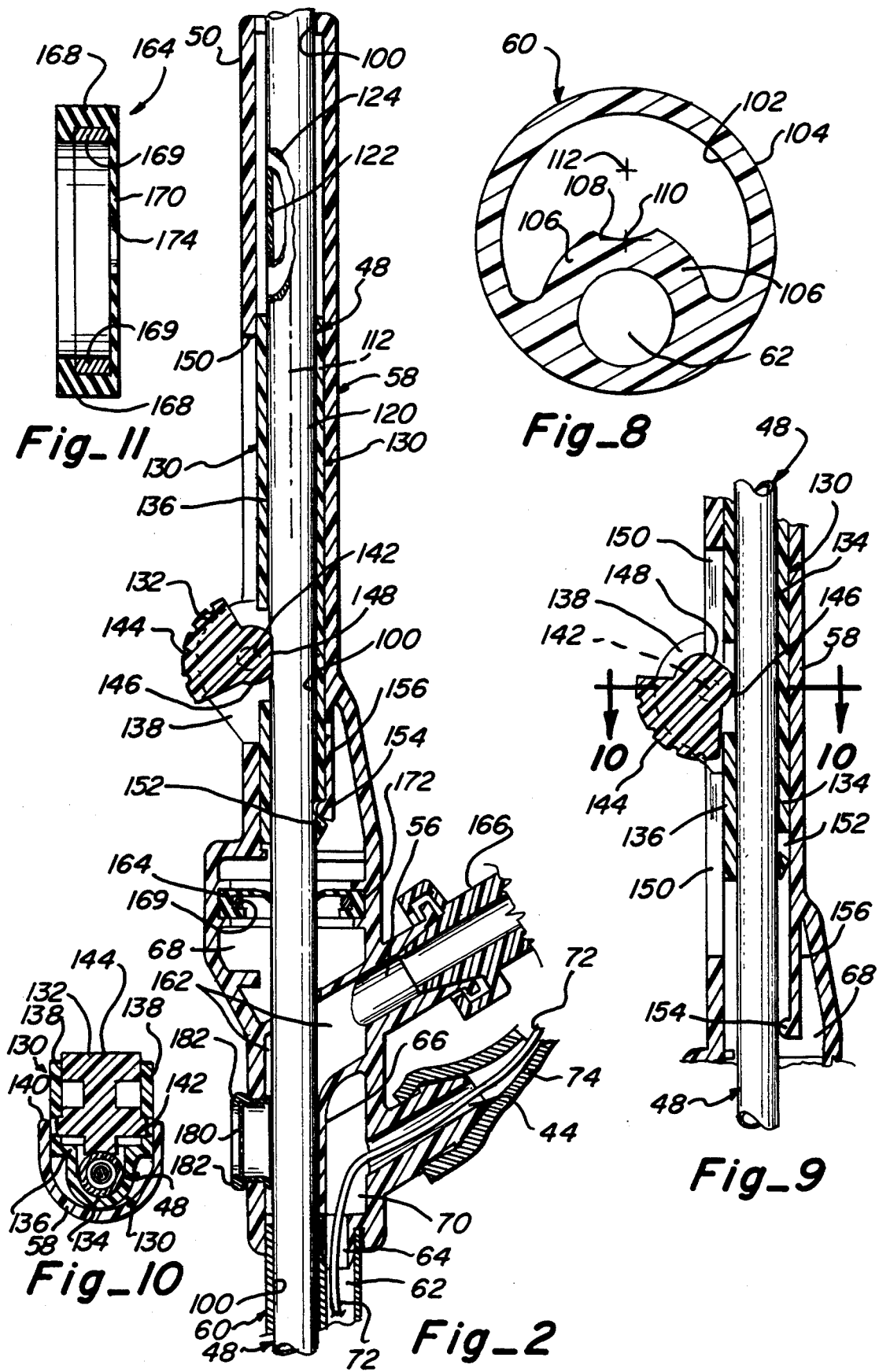

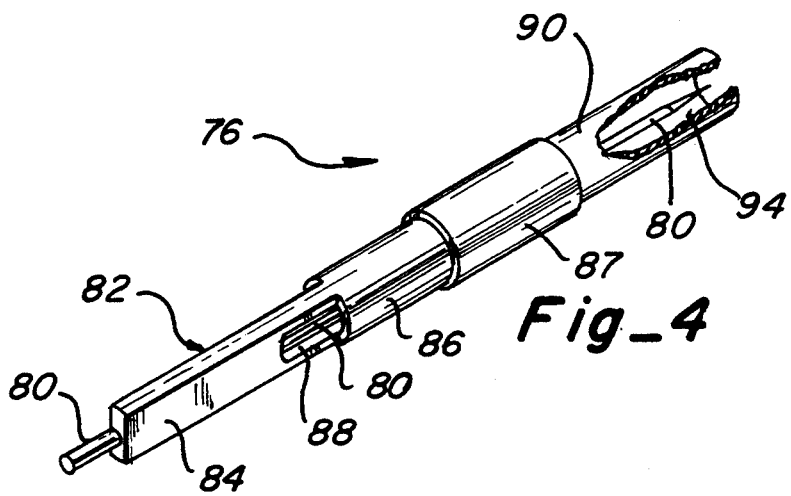
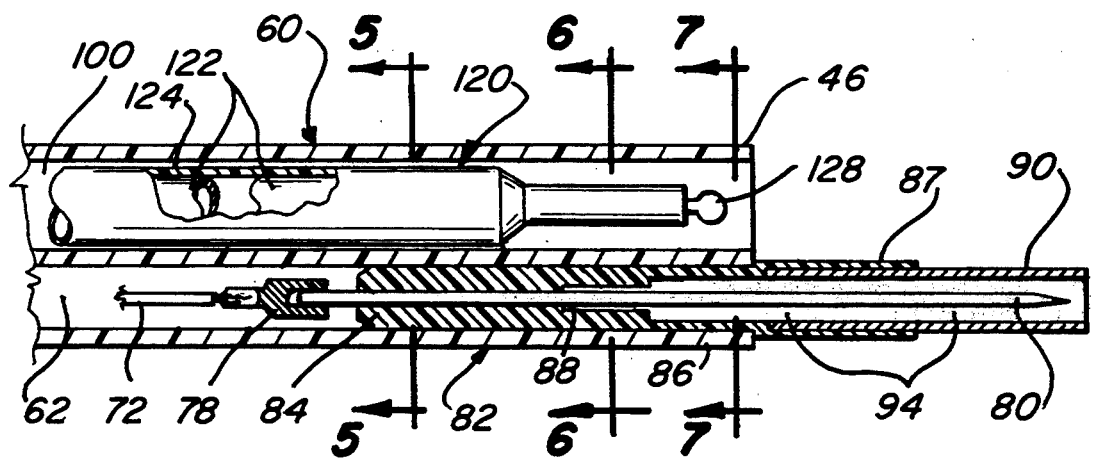
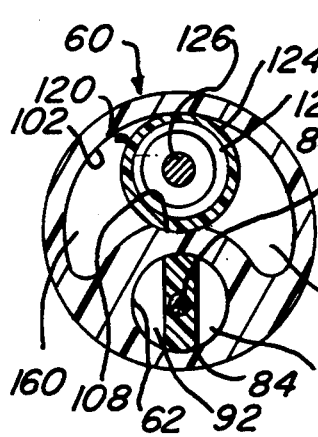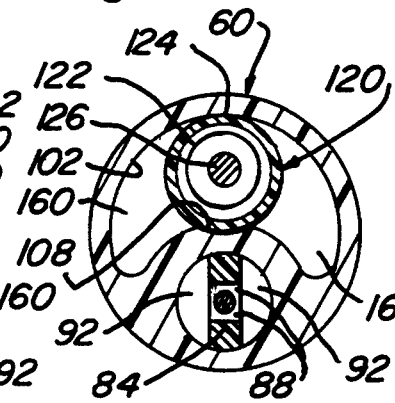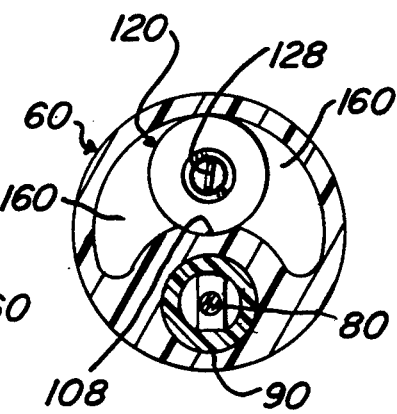

MULTIFUNCTIONAL PROBE FOR MINIMALLY INVASIVE SURGERY

This invention relates to a new and improved probe useful in minimally invasive surgery. The new and improved probe allows multiple different surgical procedures to be performed during an operation without removal of the probe from the patient. Those procedures include gas assisted electrosurgical coagulation, standard electrosurgical coagulation and cutting, laser coagulation and cutting, aqua dissection, irrigation, aspiration, evacuation, and mechanical procedures.

BACKGROUND OF THE INVENTION

At the present time, one of the most rapidly progressing areas in surgical treatment of patients is minimally invasive surgery, exemplified by laparoscopic surgery. Laparoscopic surgery, which is typically used for surgical treatment within the abdominal cavity, involves conducting the surgical procedure by use of a probe which is inserted through the abdominal wall. The probe delivers the surgical capability into the abdominal cavity. Since only a small incision needs to be made in the abdominal wall to insert the probe and gain access to the interior organs and tissues, the procedure is regarded as minimally invasive.

To gain access to the abdominal cavity, the abdominal wall is penetrated with a device called a trocar. The trocar is attached to a cannula or sheath. After penetration the trocar is withdrawn through the cannula. The abdominal cavity is then pressurized by a flow of gas delivered from an inflation pump through the cannula, and the abdominal wall expands away from the internal organs and tissues. The expansion of the abdominal wall occurs slowly and carefully so as not to damage any of the interior organs or tissues. A pressure sensor on the inflation pump senses the back pressure from the abdominal cavity and terminates the delivery of gas once the pressure reaches an upper limit. The amount of abdominal wall expansion provides good access to the interior organs.

After inflation, the probes and other surgical instruments are inserted into the abdominal cavity through a hollow interior of the cannula. A seal on the interior of the cannula contacts the probe to prevent the escape of gas from the abdominal cavity. The probes can then be manipulated from side to side due to the flexibility of the abdominal wall where the cannula penetrates it. It is typical to insert two or three cannulas in strategic locations to provide adequate access and triangulation to the inflated abdominal cavity for the surgical procedure.

A combined light source and video camera device is inserted through one of the cannulas. The interior of the abdominal cavity is illuminated and the images received by the video camera are displayed on a video monitor which is visible to the surgeon. As a result of viewing the video monitor the surgeon is able to manipulate the probes to accomplish the desired surgical effect.

After completion of the surgical procedure, the probes and cannulas are removed and the small openings made in the abdominal wall are closed. The amount of trauma experienced by the patient is considerably reduced with minimally invasive surgery, compared to the more traditional type of open surgery.

A variety of previous probes are available for use in minimally invasive surgery. However, most of these prior probes are capable of only a single use or type of functionality, for example, standard electrosurgical cutting or coagulation. A few prior art probes may be capable of limited multiple functions, such as standard electrosurgical cutting and coagulation as well as mechanical cutting or biopsy collection. Since many different types of surgical functions are typically accomplished during the minimally invasive surgery, the surgeon is usually required to remove one probe from the cannula and insert a different probe at various different stages of the procedure in order to complete the minimally invasive surgery.

Removal of one probe and insertion of another probe may have serious consequences to the patient and may, as well, create some technical difficulties. For example, if an artery or vein is cut either intentionally or accidentally during the procedure, a considerable amount of bleeding may occur into the abdominal cavity during the time while a cutting probe is removed and a standard electrosurgical coagulating probe is inserted. If the blood flow is significant, the amount of blood pooling may become substantial enough to obscure the site where the bleeding is occurring, thereby making it difficult or impossible for the surgeon to locate the bleeding site with the newly inserted probe. Furthermore the blood pool may conduct or short circuit the electrical energy applied during standard electrosurgery away from the tissue and prevent the creation and adherence of an eschar or scab in the tissue. The eschar creates the hemostasis or coagulation to stop the flow of blood. Other difficulties of a similar nature exist with respect to other types of functions which must be accomplished with single function probes used during a minimally invasive surgery.

It is with respect to this background information, as well as other information not specifically discussed here, that the present significant improvements and advancements have evolved in the field of probes for minimally invasive surgery.

SUMMARY OF THE INVENTION

An important aspect of the probe of the present invention is a nozzle and electrode assembly at a distal end of the probe. The nozzle and electrode assembly provides gas assisted electrosurgical coagulation or electro-fulguration. By incorporating the nozzle and electrode assembly in the probe, gas assisted electrofulguration is immediately available for fulguration of bleeding surfaces without the necessity of removing one probe and inserting another probe. Gas assisted electro-fulguration has inherent advantages in coagulation, because it uses gas flow to clear the surgical site of oozing and aggressively flowing blood. Thus the surface or stroma of the tissue is exposed to the electrical energy carried within the gas jet to allow the electrical energy to interact with the tissue and create an effective and adherent eschar. The blood or fluid clearing effect of the gas jet also keeps the surgical site visible, which is very important for the surgeon under the somewhat difficult and artificial circumstance of conducting the procedure by viewing a video monitor. By incorporating the nozzle and electrode assembly for gas assisted electro-fulguration in the distal end of the probe, the surgeon can immediately achieve this superior type of hemostasis, without substantial bleeding occurring before an electro-coagulation probe is inserted and positioned in the abdominal cavity or before the bleeding has become so substantial as to obscure the surgical site.

Another aspect of the probe of the present invention is the provision for a multiplicity of different types of surgical functions within a single probe. In accordance with this aspect, a separate channel extends through a tube at the distal end of the probe. The channel is adapted to receive and retain an auxiliary surgical instrument, such as a standard electrosurgical cutting or coagulation electrode, a laser fiber optic conduit by which to achieve laser cutting or coagulation, an aqua dissection conduit, or a mechanical tool such as a knife or biopsy collection device. Preferably, one auxiliary surgical instrument can be removed from the probe and a different one inserted without removal of the probe from the insufflator. Preferably, a slider or retaining member is located at a handle at a proximal end of the probe to allow adjustment of the location and position of the auxiliary surgical instrument during the procedure.

Another aspect of the probe of the present invention is at least one fluid communication passageway extending through the tube of the probe by which to irrigate fluid to the surgical site, or to aspirate fluid from the site, or evacuate fluid from within the abdominal cavity. Preferably, the irrigation, aspiration or evacuation passageway exists in addition to the channel for the auxiliary surgical instrument, and/or in addition to the nozzle and electrode assembly for gas assisted electro-fulguration. Again, the probe need not be removed to achieve irrigation, aspiration or evacuation of the abdominal cavity after or before the procedure conducted with one of the other surgical functions available from the probe.

The capability to readily exchange different auxiliary surgical instruments for use in the probe without removing the probe from the cannula, and the ability to achieve multiple different surgical functions from a single probe, contribute to the accomplishment of the procedure and the recovery of the patient. The amount of time to accomplish the surgery may be reduced if less time is consumed in exchanging probes. The multiple functions achieved by the single probe may reduce the number of cannulas which the surgeon is required to insert in the patient to accomplish the minimally invasive surgery. Of course, fewer incisions made in the patient should enhance and contribute to the patient's recovery following the surgery.

Lastly, a further aspect of the probe of the present invention is the incorporation of a pressure relief valve in communication with the passageway as a part of the probe. The pressure relief valve provides a margin of protection against the unintentional over-inflation of the abdominal cavity. Over inflation is of particular concern when using gas assisted electro-fulguration in the abdominal cavity, because previous procedures did not admit additional gas into the abdominal cavity. The back pressure sensor of the inflation pump was usually adequate in controlling the abdominal inflation pressure because any slight or momentary over-inflation would inherently leak between the abdominal wall and the cannula at the incision. However, the use of gas assisted electro-fulguration creates a situation where the gas delivered during electro-fulguration could cause a serious over-inflation situation that could not be rectified quickly enough from this inherent leakage. The pressure relief valve is important because typically there is no means to quickly relieve over-inflation. The pressure relief valve of the probe is also a back up safety mechanism for the pressure sensor of the inflation pump.

A more complete appreciation of the present invention and its scope can be obtained from understanding the accompanying drawings, which are briefly summarized below, the following detailed description of a presently preferred embodiment of the invention, and the appended claims.

BRIEF DESCRIPTION OF THE DRAWINGS

FIG. 1 is a block, schematic and perspective illustration showing the probe of the present invention in use in an abdominal cavity in association with various other equipment by which a minimally invasive surgical procedure is conducted.

FIG. 2 is an longitudinal cross-section of a handle of the probe shown in FIG. 1 at a proximal end of the probe.

FIG. 3 is an enlarged longitudinal cross-section of a tube of the probe shown in FIG. 1 at a distal end of the probe.

FIG. 4 is a perspective view of a nozzle and electrode assembly at the distal end of the probe shown in FIG. 3.

FIG. 5 is a cross-section view taken substantially in the plane of line 5—5 of FIG. 3.

FIG. 6 is a cross-section view taken substantially in the plane of line 6—6 of FIG. 3.

FIG. 7 is a cross-section view taken substantially in the plane of line 7—7 of FIG. 3.

FIG. 8 is an enlarged cross-sectional view of only the tube of the probe, similar to the views of the tube shown in FIGS. 5, 6 and 7.

FIG. 9 is an enlarged view of a portion of the handle of the probe shown in FIG. 2 illustrating details of a slider member.

FIG. 10 is a cross-sectional view taken substantially in the line of plane 10—10 in FIG. 9.

FIG. 11 is an enlarged view of a seal located within the handle of the probe shown in FIG. 2.

DETAILED DESCRIPTION

A presently preferred embodiment and best mode presently known for practicing the present invention is a probe 20 shown in FIG. 1. The probe 20 is shown as it would typically be used in a minimally invasive surgical procedure in an abdominal or body cavity 22. The probe 20 is inserted into the abdominal cavity through a cannula 24 which has previously been passed through the abdominal body or wall 26. An inflation pump 28 forces pressurized and sterile gas, such as carbon dioxide, through the cannula 24 into the abdominal cavity 22. As a result, the abdominal wall 26 expands away from the interior tissues and abdominal organs 30. A pressure sensor of the inflation pump 28 controls the operation of the pump 28 to limit the amount of pressure within the abdominal cavity 22 and thereby limits the amount of expansion of the abdominal wall 26. A second cannula 34, and possibly others as determined by the surgeon, is also positioned in the abdominal wall 26, but the additional cannulas are not necessarily attached to the inflation pump 28.

A video camera and light source device 36 is connected to a wand-like device 38. The wand-like device 38 is inserted into the abdominal cavity 22 through the cannula 34. The light source of the device 36 illuminates the interior tissues and organs 30, and the video camera of the device 36 transmits video images to a video monitor 40. By viewing the interior organs 30, the surgeon is able to manipulate the probe 20 to achieve a desired surgical effect.

The probe 20 is connected to a gas assisted electro-fulguration device 42. The gas assisted electro-fulguration device 42 is represented by the type of equipment described in U.S. Pat. No. 4,781,175 granted Nov. 1, 1988 for "Electrosurgical Conductive Gas Stream Technique of Achieving Improved Eschar for Coagulation" which is owned by the assignee hereof. Other U.S. patents and applications pertinent to gas assisted electro-fulguration include U.S. Pat. No. 4,901,720 granted Feb. 20, 1990 for "Power Control for Beam-Type Electrosurgical Unit," U.S. Pat. No. 4,901,719 granted Feb. 20, 1990 for "Electrosurgical Conductive Gas Stream Equipment" and application Ser. No. 592,810, filed Oct. 4, 1990, for "Electrosurgical Handpiece Incorporating Blade and Conductive Gas Functionality."

In general, gas assisted electro-fulguration involves the delivery of a stream or jet of inert gas to the tissue at a surgical site while simultaneously transmitting electrical energy as arcs in ionized conductive pathways in the flowing gas jet. The interaction of the gas flow and the electrical arcs achieve a superior coagulative or hemostatic effect on bleeding tissue surfaces. Gas assisted electro-fulguration is particularly useful and effective on aggressively bleeding surfaces because the gas is able to hold off and displace the blood from the surface of the tissue to allow the arcs of electrical energy carried in the gas to interact more thoroughly and effectively with the tissue. A more effective eschar is created which is less susceptible to floating away due to a lack of adherence to the underlying tissue. The gas assisted electro-fulguration device 42 shown in FIG. 1 is both the source of gas and the source of electrical energy, and both the gas and the electrical energy is supplied to the probe 20 at a gas electrosurgical port 44. The electro-fulguration effect is created at a front or distal end 46 of the probe 20.

The probe 20 also offers the capability of accepting and utilizing a variety of auxiliary surgical instruments 48, such as a standard electrosurgical cutting and coagulation electrode, a laser fiber optic conduit for cutting and coagulation, an aqua dissection conduit, mechanical tools such as a knife or a biopsy collection device, and other types of surgical equipment. The auxiliary surgical instruments can be inserted into the probe 20 from its rear or proximal end 50, or when the probe is removed from the cannula, from the distal end 46. Depending on the type of auxiliary surgical instrument 48 used with the probe 20, the instrument 48 may need to be connected to support equipment 52 by which to use the auxiliary surgical instrument 48. For example, if the instrument 48 is a standard electrosurgical electrode, the support equipment will be a standard electrosurgical generator. When a laser fiber optic conduit is used as the auxiliary surgical instrument with the probe 20, the laser fiber optic conduit will be connected to a laser beam device. When an aqua dissection conduit is used as the auxiliary surgical instrument, the aqua dissection conduit will be connected to a fluid pressure and flow generation device. Of course, if a mechanical tool is used as the auxiliary surgical instrument, it may or may not be connected to support equipment, since manual control of many mechanical tools by the surgeon will operate them without additional support equipment.

Another feature of the multifunctional probe 20 is the capability to achieve irrigation, aspiration or evacuation within the abdominal cavity from the distal end 46 of the probe. As will be understood more completely from the following description, the irrigation, aspiration or evacuation is achieved by fluid flow to or from the distal end 46 of the probe 20. A fluid flow control device 54 is connected to a fluid flow port 56 of the probe 20 to achieve the irrigation, aspiration or evacuation.

As a result of the images on the video monitor 40 obtained from the video camera of the device 36, the surgeon can grasp a handle 58 of the probe 20 and manipulate a connected tube 60 of the probe 20 to position the distal end 46 at the desired location to achieve the desired surgical effect on the tissue or organs 30. The probe is pivoted along with the cannula 24 at the point where both extend through the abdominal wall to move the distal end 46 to the desired location.

The handle 58 and the tube 60 are permanently connected together as a unitary structure by an adhesive or the like, and the handle 58 and the tube 60 are the two major elements of the probe 20. Preferably the handle 58 and the tube 60 and all of the components associated with these elements other than the metallic and elastomeric components are formed of plastic, to obtain a relatively inexpensive and disposable probe 20. Of course, the probe 20 could also be formed of more long lasting and durable materials which are capable of repeated sterilizations, in order to allow the probe 20 to be used repeatedly before disposal.

More details concerning the gas assisted electro-fulguration aspects of the probe 20 are illustrated in FIGS. 2 through 8. A cylindrical conduit 62 extends longitudinally completely through the tube 60 from the handle 58 to the distal end 46, as is understood from FIGS. 1, 2 and 3. With the tube 60 attached to the handle 58, the conduit 62 fits over a tubular sleeve 64 formed in the forward end of the handle 58. A divider or wall 66 within a hollow interior 68 of the handle 58 defines a communication pathway 70 between the conduit 62 and the gas electrosurgical port 44. An electrical conductor 72 extends through the conduit 62, the pathway 70 and out of the port 44 to the gas assisted electro-fulguration device 42. Electrical energy for electro-fulguration is supplied to the probe 20 over the conductor 72. A flexible tubing 74 is connected from the port 44 to the gas assisted electrocoagulation device 42 by which gas for electro-fulguration is supplied to the probe 20 and the conduit 62.

At the distal end 46 of the probe, a nozzle and electrode assembly 76 is retained in the conduit 62, as is shown in FIGS. 3 and 4. The conductor 72 extends the length of the conduit 62 and is electrically connected by a connector 78 to the rear end of an elongated electrode 80 of the assembly 76. The rear end of the electrode 80 is retained in the assembly 76 by a support structure 82. Due to the retention of the electrode 80 at the rear end thereof, the electrode projects forward in a cantilever supported manner. A rear portion 84 of the support structure 82 is generally rectangularly shaped, and the rectangularly shaped portion 84 fits within the conduit 62 as is shown in FIGS. 4 and 5. A midsection 86 of the support structure 82 is generally tubularly shaped, hollow and integral with the rectangularly shaped portion 84. At the forward end of the rectangular portion 84, slots 88 are formed transversely through the portion 84 to achieve a pathway into the hollow interior of the tubular midsection 86 and to expose the electrode 80, as is shown in FIG. 6. A receptacle portion 87 extends forward from the midsection 86. A hollow sleeve 90 is partially received within the receptacle portion 87, but the sleeve is of sufficient length to extend forward beyond the end of the receptacle portion 87. The midsection 86 and the sleeve 90 surrounds the exposed forward projecting portion of the electrode 80. Both the sleeve 90 and the forward tip of the electrode 80 terminate at approximately the same location as shown, or alternatively, the electrode tip is slightly recessed within the sleeve 90.

Preferably, the support structure 82 is formed of plastic, the electrode 80 is metallic such as tungsten, and the sleeve 90 is ceramic. Preferably the electrode 80 and the sleeve 90 are insert molded during the formation of the plastic support structure 82. The nozzle and electrode assembly 76 is retained within the conduit 62 due to a friction fit, but an adhesive may also be employed to connect the assembly to the tube 60. If the sleeve 90 is not insert molded to the receptacle 87, an adhesive may be used to hold these elements together. In some circumstances, it may be possible to eliminate the receptacle 87 and rely on the retention of the support structure 82 and a portion of the sleeve within the conduit 62 (not shown) to hold these elements together.

Two oppositely oriented D-shaped openings 92 result on the opposite sides of the rectangularly shaped portion 84 when it is inserted in the conduit 62, as is shown in FIGS. 5 and 6. It is through these D-shaped openings 92 that gas is conducted from the conduit 62 into the slots 88 and into a cylindrical center opening 94 formed by the interiors of the hollow midsection 86 and the sleeve 90, as is shown in FIGS. 3 and 7. The cylindrical center opening 94 is preferably concentric with the electrode 80. The center opening through the sleeve 90 forms a nozzle for the gas to exit the assembly 76. Before exiting the nozzle, the gas surrounds the exposed electrode 80 and becomes ionized as it traverses through the nozzle as a result of the electrical potential applied on the electrode 80 from the conductor 72. The ionized gas conducts the electrical energy from the electrode 80 in arcs within the gas flowing from the nozzle to the tissue to achieve electro-fulguration.

In addition to the conduit 62, the tube 60 also includes an instrument channel 100 which extends parallel to the conduit 62 along the length of the tube. The instrument channel 100 communicates directly with the interior 68 of the handle 58 as is shown in FIG. 2. The channel 100 extends continuously and longitudinally through the probe 20 from the distal end 46 at the tube 60 to the proximal end 50 at the handle 58. It is through this channel 100 that the various auxiliary surgical instruments are utilized in conjunction with the probe 20.

The auxiliary surgical instrument should be generally elongated and have an exterior cylindrical shape to fit within the channel 100. As is shown in FIG. 8, a cross sectional view of the channel 100 reveals a crescent shaped configuration. An inner cylindrical wall 102 of the tube 60 is generally parallel to the outer cylindrical wall 104 of the tube 60. An inner partition 106 within the tube projects radially inward from both points at which the inner cylindrical wall 102 terminates. The partition 106 separates the conduit 62 from the channel 100 along with the length of the tube 60. The partition 106 has a cylindrically curved support surface 108 which faces radially outward. The inner most location of concavity of the support surface 108 is at the central axis 110 of the tube 60. The curvature of the support surface 108 is defined by an equal length radius from a point 112 which is midway between the axis 110 of the tube and the inner cylindrical wall 102. The point 112 is located at the longitudinal axis of the auxiliary surgical instrument.

Having the shapes thus described, a longitudinal auxiliary surgical instrument having a diameter slightly less than the distance between the axis 110 and the wall 102 will fit within the instrument channel 100 and be supported by and retained in position when it rests on the support surface 108 and the interior surface 102, as is shown in FIGS. 3, 5, 6 and 7. The longitudinal axis of the instrument channel 100 becomes the same as the longitudinal axis of the auxiliary surgical instrument, and both axes are located at the point 112. Because the support surface 108 curves radially outward from the axis 110 of the tube 60 and toward the interior cylindrical wall 102, the cylindrically shaped surgical instrument will be prevented from moving transversely within the instrument channel 100. The support surface 108 and the interior surface 102 are one example of means for supporting the auxiliary surgical instrument in the channel 100, however other types and configurations of support means, either integral with the tube 60 or separate components, may be used as alternatives.

Although a variety of different types of auxiliary surgical instruments which have the necessary outer diameter and the general cylindrical shape can be used with the probe 20, an exemplary standard electrosurgical coagulation and cutting electrode 120 is illustrated in FIGS. 1, 2, 3, 5 and 6 as the auxiliary surgical instrument 48. The electrosurgical electrode 120 is formed from a hollow metallic tube 122 upon which an exterior layer of insulating material 124 such as heat shrink tubing is connected. The tube 122 is preferably formed from stainless steel or aluminum. At the proximal end of the electrode 120, a metallic terminal end 126 (FIG. 1) is mechanically and electrically connected to the tube 122. The terminal end 126 allows an electrical conductor connected to a conventional electrosurgical generator to be connected to the electrode 120 as the support equipment 52 (FIG. 1). At the distal end of the electrode 120 a metallic operating tip 128 is mechanically and electrically connected to the tube 122. The tip 128 may be of a variety of configurations adapted for the particular surgical procedure which the surgeon desires to accomplish. So long as the tip 128 extends no further transversely outward at any location than the exterior surface of the electrode 120, the electrode 120 can be inserted and removed from the channel 100 from the proximal end of the probe 20, while the probe is in place in the abdominal cavity 22 (FIG. 1). If the operating tip 128 is larger than the exterior surface of the electrode 120, the auxiliary surgical instrument must be inserted in the instrument channel 100 before the probe is inserted in the cannula 24 (FIG. 1).

To allow the surgeon to control the extension and retraction of the auxiliary surgical instrument 48, such as the electrode 120, without moving the probe within the cannula 24 (FIG. 1), the probe 20 includes a slider member 130, which is shown in FIGS. 2, 9 and 10. The slider member 130 is movably retained within the interior 68 of the handle 58, to allow longitudinal movement along the instrument channel 100. The auxiliary surgical instrument 48 extends through a slot 134 in the slider member 130 and a lock roller member 132 applies frictional retaining force by which to selectively retain the slider member to the auxiliary surgical instrument 48. Once the slider member and the auxiliary surgical instrument are retained together, longitudinal movement of the slider member extends or retracts the distal end of the auxiliary surgical instrument from the end of the instrument channel at the distal end 46 of the probe 20.

The slot 134 of the slider member 130 in which the auxiliary surgical instrument is retained has a U-shaped configuration which extends continuously longitudinally along and forms a part of the instrument channel 100. An inner cylindrical surface of the U-shaped slot 134 is of uniform radius from the instrument axis (FIG. 10). The straight leg portions of the U-shaped slot 134 integrally connect to a base portion 136 of the slider member 130. The base portion 136 extends the length of the slider member 130. A transversely center point on the bottom surface of the base portion 136 is located at approximately the same distance from the instrument axis 112 as the curved surface of the U-shaped slot 134, thus allowing the auxiliary surgical instrument to closely fit within the U-shaped slot 134.

At a middle longitudinal location along the length of the slider member 130, a pair of wing portions 138 extend upward from opposite transverse sides of the base portion 136. The wing portions 138 each have an opening 140 formed therein for receiving a rotational axle 142 of the lock roller 132. The axle 142 of the lock roller 132 is snapped into the openings 140 by slightly spreading the wing portions 138 and sliding the lock roller 132 between them until the axle 142 enters the openings 140. The resiliency of the wing portions returns them to the original position to hold the lock roller in position. As an alternative, the axle may not be made integral with the lock roller, but instead, a hole (not shown) may be formed through the lock roller at the location of the axle. A brass or other type of pin (also not shown) will be inserted through this hole and the openings 140 to hold the lock roller in a pivotably connected condition to the wing portions. Use of the separate pin avoids the necessity to obtain sufficient resilience from the wing portions to allow them the accept the integral axle as shown.

The lock roller 132 includes an upper surface 144 which extends above the wing portions 138. The upper surface 144 has transverse slots or other types of ridges or indentions formed therein by which the surgeon can adequately frictionally engage the surface 144 and rotate the lock roller 132 about the axle 142.

A cam surface 146 is eccentrically positioned relative to the axle 142 at the lower end of the lock roller 132. By rotating the lock roller 132 in a clockwise direction as illustrated in FIGS. 2 and 9, the cam surface 146 applies lateral force on the auxiliary surgical instrument 48 located within the U-shaped slot 134 of the slider member 130. Upon achieving a predetermined rotational position, a flat surface 148 of the cam surface 146 contacts the outer exterior of the auxiliary surgical instrument 48 and causes the lock roller 132 to be retained in position.

The amount of eccentric movement of the cam surface 146 and the flat surface 148 is sufficient to frictionally retain the auxiliary surgical instrument in the U-shaped slot 134 so that the instrument 48 moves in conjunction with the slider member 130. Thus, the extension and retraction of the operating tip of the auxiliary surgical instrument at the distal end of the probe is achieved by moving the slider member 130 forward and backward. As is shown in FIGS. 2 and 9, an opening 150 is formed in the housing 58 to allow the lock roller 132 and wing portions 138 to move forward and rearwardly on the exterior of the handle 58.

The lock roller 132 is one of many alternative examples of a retaining means for selectively retaining the auxiliary surgical instrument to the slider member. Virtually any type of controllable retaining device capable of achieving a sufficient frictional engagement with the auxiliary surgical instrument to cause it to move with the slider member will suffice as an alternative to the lock roller 132.

Should the surgeon desire to fix the slider member 130 in a single location relative to the housing 58, the forward lower end of the U-shaped slot 134 has formed therein a notch 152 which is adapted to receive a ridge 154 of a resilient tang 156 located within the interior 68 of the handle 58, as is shown in FIGS. 2 and 9. The resilient tang 156 deflects toward and away from the slider member and transversely with respect to the instrument channel 100, to allow the ridge 154 to snap within the notch 152 when the slider member 130 is moved to the forward position within the opening 150. With the ridge 154 engaged in the notch 152, the slider member 130 and the retained auxiliary surgical instrument 48 are held in a fixed position relative to the handle 58 of the probe 20. This feature allows the surgeon to fix the desired amount of extension of the auxiliary surgical instrument from the distal end 46 of the probe. By releasing the lock roller 132, adjusting the position of the auxiliary surgical instrument by grasping it from the rear end of the housing 58, and then rotating the lock roller 132 back into the retaining position, the position of the auxiliary surgical instrument in the probe 20 is changed. Alternatively, the surgeon can extend and retract the auxiliary surgical instrument by longitudinal movement of the slider member 130, provided that the slider member is not moved forward to the retained position.

It is preferred to arrange the cam surface 146 and the flat surface 148 to achieve retention between the slider member and the auxiliary surgical instrument 48 due to clockwise movement of the lock roller as shown in FIGS. 2 and 9. Clockwise movement of the lock roller results from finger force which has a component tending to move the slider member rearward. Since a rearward component of finger force is required to overcome the force of the tang 156 to move the slider member rearward from the forwardmost position, the lock roller will not rotate to accidentally release the auxiliary surgical instrument when the slider member is moved rearward from the forward most position.

In order to irrigate, aspirate and evacuate fluid (gas or liquid) from within the abdominal cavity and at the surgical site, the probe includes at least one passageway extending through the tube 60 to the distal end 46. The embodiment of the probe 20 shown actually includes two passageways 160 as is shown in FIGS. 5, 6 and 7. The passageways 60 extend through the tube 160 on each side of the auxiliary surgical instrument 48, represented by the electrode 120, and communicate with a chamber 162 formed in the interior 68 of the handle 58, as shown in FIG. 2. The rear end of the chamber 162 is closed by a seal 164. The divider 66 separates the chamber 162 from the pathway 70. The chamber 162 communicates with the fluid flow port 56. A standard luer fitting 166 is connected to the end of the port 56, and a hose or other tubular conduit connects the fluid flow control device 54 (FIG. 1) to the probe 20 at the luer fitting.

As is shown in FIGS. 5, 6 and 7, a longitudinal seal is established between the auxiliary surgical instrument and the interior surface 102 and the support surface 108. This seal is maintained during the linear movement of the auxiliary surgical instrument within the channel 100. Consequently, the remainder of the space within the channel 100 not occupied by the auxiliary surgical instrument becomes the passageways 160. It is through these passageways 160 that the fluid flow derived from the flow control device 54 (FIG. 1) achieves irrigation, aspiration, and evacuation within the abdominal cavity.

The seal 164 is one example of a sealing means for providing a fluid seal between the auxiliary surgical instrument 48 and the interior 68 of the handle 58. Consequently, the fluid within the abdominal cavity, whether it be liquid or gas, is confined within the interior chamber 162 for communication into and out of the fluid flow port 56. The seal 164 prevents the fluid from entering the other portions of the handle 58 and interfering with the movement of the slider member 130, for example.

The seal 164 is illustrated in FIG. 11 to include an outer relatively thick edge 168 from which there extends inwardly a relatively thin membrane 170. The edge 168 fits within a retention receptacle 172 formed within the interior of the handle 58, as is shown in FIG. 2. A plastic ring 169 contacts the edge 168 and expands the edge 168 outward to hold the seal in position in the receptacle 172. At the center of the membrane 170, a circular opening 174 is formed for the purpose of receiving the generally circular exterior configuration of the auxiliary surgical instruments 48. The opening 174 is located at the axial center 112 of the auxiliary surgical instrument and the channel 100. The seal 164 is preferably formed of a resilient elastomeric material, and the deflection, flexibility and resilience of the membrane 170 achieves the fluid tight seal against the exterior surface of the auxiliary surgical instrument, as shown in FIG. 2. The membrane 170 thus resists the passage of the fluid into or out of the interior chamber 162 from around the auxiliary surgical instrument, and confines all fluid flow through the port 56. By orienting the seal 164 with the edge 168 projecting forwardly, the interior pressure within the chamber 162 forces the edges 168 radially outward, thereby providing a more effective seal of the edges 168 against the retention receptacle 172. The ring 169 is preferably formed of more rigid plastic material. Other types of sealing means which provide the equivalent functionality for confining the fluid in the interior chamber 162 might serve as alternatives to the seal 168 described above.

Another important feature of the probe 20 is the provision of a pressure relief valve 180 connected in fluid communication with the interior chamber 162. The pressure relief valve 180 is retained in a receptacle 182 formed in the handle 58, and is operative to vent pressurized fluid within the interior chamber 162 to the exterior of the handle upon the pressure of the fluid exceeding a predetermined level. The pressure relief valve 180 is particularly useful in preventing over inflation of the abdominal cavity during gas assisted electro-fulguration. The gas added to the abdominal cavity during electro-fulguration contributes to the pressure in the abdominal cavity. Although the back pressure sensor of the inflation pump (28, FIG. 1) may terminate the delivery of gas from the inflation pump to the abdominal cavity, the gas from the gas assisted electro-fulguration may continue to expand the abdominal wall. The limited venting from the incision around the cannula is typically not sufficient to prevent over-pressurization during gas assisted electro-coagulation, but the pressure relief valve 180 will relieve this additional pressure once it exceeds the release point of the pressure relief valve 180. Since the interior chamber 162 communicates with the abdominal cavity 22 (FIG. 1) through the passageways 160 (FIGS. 5-7), the pressure relief valve 180 acts as an auxiliary or back up for the proper functionality of the back pressure sensor associated with the inflation pump 28 (FIG. 1). The incorporation of the pressure relief valve 180 in the probe 20 thus increases the measure of safety against the accidental over pressurization of the abdominal cavity during a minimally invasive surgery. The general nature of pressure relief valves is well known.

By providing a cylindrical cross sectional channel extending from one end of the probe to the other along the instrument channel 100, it is apparent that the surgeon may exchange or substitute one auxiliary surgical instrument 48 for another by releasing the lock roller 132 and withdrawing the instrument during the procedure. Of course, for the slight amount of time during which one auxiliary surgical instrument is withdrawn and before another can be inserted in the probe, there will be a slight leak of gas through the relatively small opening 174 in the seal 168. This slight leak of gas over a relatively short duration of time should not be sufficient to result in any significant reduction in the expansion of the abdominal wall, particularly since the inflation pump 28 (FIG. 1) should become operative immediately to add additional gas to the abdominal cavity to counteract the escaping gas. The longitudinal arrangement of the instrument channel in the manner described provides the substantial advantage of the surgeon not having to withdraw the probe from the cannula to exchange auxiliary surgical instruments which have operating tips that do not exceed the outside dimensions of the instrument. Of course auxiliary surgical instruments which do have larger operating tips can be inserted from the distal end of the probe prior to insertion in the cannula.

Of course, one of the substantial advantages offered by the probe 20 is the capability of instantly obtaining gas assisted electro-fulguration when necessary. The availability of gas assisted electro-fulguration greatly reduces the risk of immediate and serious bleeding before the surgeon is able to control it by other conventional means. Of course, a sufficient amount of bleeding can greatly obstruct the surgical site and inhibit the further progress of the procedure, particularly if it becomes necessary to remove one probe, insert another probe to attempt to control the bleeding, remove that probe, and insert yet another probe to evacuate the blood which accumulated before the bleeding was controlled. With the probe of the present invention, all of these functions can be achieved by use of the single probe in a relatively rapid manner to continue the progress of the procedure without the substantial delays or impediments which were previously typical in minimally invasive surgeries due to the need to use separate surgical probes to achieve the multiplicity of surgical functions encountered.

A presently preferred embodiment of the present invention and many of its improvements have been described with a degree of particularity. This description has been made by way of preferred example and is based on a present understanding of knowledge available regarding the invention. It should be understood, however, that the scope of the present invention is defined by following claims, and not necessarily by the detailed description of the preferred embodiment.

The invention claimed is:

1. A probe for performing minimally invasive surgery through a cannula extending through a body wall of a patient and into a body cavity where the surgery is performed, comprising:

a handle at a proximal end of the probe;

an elongated tube connected to the handle and extending to a distal end of the probe, the tube including a conduit and an electrical conductor which both extend along the length of the tube;

an assembly of a gas nozzle and an electrode positioned within the nozzle, the nozzle and electrode assembly connect to the tube at the distal end of the probe, the conduit communicating gas to the nozzle during gas assisted electro-fulguration, the electrical conductor is connected to the electrode for conducting electrical energy to the electrode during gas assisted electro-fulguration; and the tube and the nozzle and electrode assembly having a predetermined configuration to permit the tube and the nozzle and electrode assembly to be inserted through the cannula and into the body cavity, the connection of the handle to the tube permitting the distal end to be positioned at a surgical site within the body cavity by manipulation of the handle.

2. A probe for performing minimally invasive surgery through a cannula extending through a body wall of a patient and into a body cavity where the surgery is performed, comprising:

a handle at a proximal end of the probe;

an elongated tube connected to the handle and extending to a distal end of the probe, the tube including a conduit and an electrical conductor which both extend along the length of the tube, the tube having a predetermined configuration to permit the tube to be inserted through the cannula and into the body cavity, and the tube further having a predetermined length which is sufficient to extend the distal end 0f the probe through both the cannula and an open space within the body cavity to reach a surgical site within the body cavity and perform the surgery;

an assembly of a gas nozzle and an electrode positioned within the nozzle, the nozzle and electrode assembly retained in the conduit within the tube at the distal end of the probe, the conduit communicating gas to the nozzle during gas assisted electro-fulguration, the electrical conductor connected to the electrode for conducting electrical energy to the electrode during gas assisted electro-fulguration; and the nozzle and electrode assembly further comprises:

an elongated electrode;

a support structure connected to a rear end of the electrode and supporting the electrode in a forward projecting cantilever manner with a forward portion of the electrode exposed to gas flow therearound; and a hollow sleeve connected to the support structure and surrounding the forward exposed portion of the electrode, an interior of the hollow sleeve forming the nozzle.

3. A probe as defined in claim 2, wherein:

the support structure further includes an opening for conducting gas from the conduit into the interior of the sleeve.

4. A probe for performing minimally invasive surgery through a cannula extending through a body wall of a patient and into a body cavity where the surgery is performed, comprising:

a handle at a proximal end of the probe;

an elongated tube connected to the handle and extending to a distal end of the probe, the tube including a conduit and an electrical conductor which both extend along the length of the tube, and the tube having a predetermined configuration to permit the tube to be inserted through the cannula and into the body cavity;

an assembly of a gas nozzle and an electrode positioned within the nozzle, the nozzle and electrode assembly connected to the tube at the distal end of the probe, the conduit communicating gas to the nozzle during gas assisted electro-fulguration, the electrical conductor connected to the electrode for conducting electrical energy to the electrode during gas assisted electro-fulguration; and the tube further comprises a passageway separate from the conduit and the nozzle, said passageway extending along the length of the tube and communicating fluid with the distal end of the probe during a procedure involving the application of at least one of evacuation, irrigation or aspiration during the surgery in which gas assisted electro-fulguration is applied from the nozzle and electrode assembly.

5. A probe as defined in claim 4, wherein:

the handle has a hollow interior;

the passageway extends into the hollow interior of the handle; and the handle includes a fluid flow port communicating with the hollow interior and with the passageway for establishing fluid communication between the fluid flow port and the passageway.

6. A probe as defined in claim 5, wherein:

the conduit communicates with the hollow interior of the handle;

the handle includes a gas electrosurgical port communicating with the hollow interior of the handle and with the conduit to establish gas communication from the gas electrosurgical port through the conduit to the nozzle and electrode assembly; and the hollow interior of the handle includes a divider to divide the interior of the handle into a first fluid communication pathway and a second fluid communication pathway, the first fluid communication pathway extending between the gas electrosurgical port and the conduit in the tube, and the second separate fluid communication pathway extending between the fluid flow port and the passageway, the first and second fluid communication pathways being separate of one another.

7. A probe as defined in claim 6, wherein:

the conductor extends through the conduit and the first fluid communication pathway and the gas electrosurgical port.

8. A probe for performing minimally invasive surgery through a cannula extending through a body wall of a patient and into a body cavity where the surgery is performed, comprising:

a handle at a proximal end of the probe;

an elongated tube connected to the handle and extending to a distal end of the probe, the tube including a conduit and an electrical conductor which both extend along the length of the tube, and the tube having a predetermined configuration to permit the tube to be inserted through the cannula and into the body cavity;

an assembly of a gas nozzle and an electrode positioned within the nozzle, the nozzle and electrode assembly connected to the tube at the distal end of the probe, the conduit communicating gas to the nozzle during gas assisted electro-fulguration, the electrical conductor connected to the electrode for conducting electrical energy to the electrode during gas assisted electro-fulguration; and the tube further includes means for supporting an elongated auxiliary surgical instrument for longitudinal movement along the tube at the distal end of the probe.

9. A probe for performing minimally invasive surgery through a cannula extending through a body wall of a patient and into a body cavity where the surgery is performed, comprising:

a handle at a proximal end of the probe;

an elongated tube connected to the handle and extending to a distal end of the probe, the tube including a conduit and an electrical conductor which both extend along the length of the tube, and the tube having a predetermined configuration to permit the tube to be inserted through the cannula and into the body cavity;

an assembly of a gas nozzle and an electrode positioned within the nozzle, the nozzle and electrode assembly connected to the tube at the distal end of the probe, the conduit communicating gas to the nozzle during gas assisted electro-fulguration, the electrical conductor connected to the electrode for conducting electrical energy to the electrode during gas assisted electro-fulguration; and a channel extending longitudinally through the tube and into the handle, the channel adapted to accept an elongated auxiliary surgical instrument.

10. A probe as defined in claim 9, wherein the channel is adapted to accept an auxiliary surgical instrument selected from a group consisting of a standard electrosurgical electrode, a laser fiber optic conduit, an aqua dissection conduit, and a mechanical tool.

11. A probe as defined in claim 9, wherein:
the channel extends longitudinally through the tube and the handle between the proximal and distal ends of the probe to allow the replacement of one auxiliary surgical instrument with another auxiliary surgical instrument from the proximal end of the probe.

12. A probe as defined in claim 9, further comprising:
a slider member connected to the handle and moveable along the channel; and
retaining means connected to the slider member and operative for selectively retaining an auxiliary surgical instrument to the slider member to achieve movement of the auxiliary surgical instrument with movement of the slider member.

13. A probe as defined in claim 12, wherein:
the slider member includes an elongated slot forming a part of the channel and adapted for receiving the auxiliary surgical instrument.

14. A probe as defined in claim 13, wherein the retaining means comprises:

a pivotable member pivotably connected to the slider member and having an eccentric surface moveable into the slot for contacting the auxiliary surgical instrument when the pivotable member is pivoted.

15. A probe as defined in claim 14, wherein:
the pivotable member comprises a lock roller, and the eccentric surface includes a flat surface to hold the lock roller in a retaining position against the auxiliary surgical instrument.

16. A probe as defined in claim 9, further comprising:
means connected to the tube for supporting and retaining an auxiliary surgical instrument within the channel to allow longitudinal sliding movement of the auxiliary surgical instrument along the channel.

17. A probe as defined in claim 16, wherein:
the handle has a hollow interior;
the tube further comprises a passageway extending along the length of the tube and communicating with the hollow interior of the handle; and
the handle includes a fluid flow port communicating with the hollow interior and with the passageway for establishing fluid communication between the fluid flow port and the distal end of the probe through the passageway during a procedure involving the application of at least one of evacuation, irrigation or aspiration during the surgery.

18. A probe as defined in claim 17, wherein:
the channel defines the passageway extending along and parallel to an auxiliary surgical instrument which is retained and supported in the channel.

19. A probe as defined in claim 18, wherein:
the channel is defined by an interior surface of the tube;
the auxiliary surgical instrument includes a substantially cylindrical exterior surface;
the means for supporting and retaining the auxiliary surgical instrument within the channel comprises a curved support surface which contacts the exterior cylindrical surface of the auxiliary surgical instrument; and
the passageway exists between the exterior surface of the auxiliary surgical instrument and the interior surface of the tube.

20. A probe as defined in claim 19, wherein:
the support surface and the exterior cylindrical surface of the auxiliary surgical instrument have approximately the same curvature;
the auxiliary surgical instrument is supported between the curved support surface and the interior surface of the tube along a longitudinal contact position which is opposite the support surface; and
the interior surface of the tube has a lesser degree of curvature than the exterior surface of the auxiliary surgical instrument along the longitudinal contact position.

21. A probe as defined in claim 20, wherein:
the support surface extends along substantially the full length of the tube.

22. A probe as defined in claim 21, wherein:
the longitudinal contact position extends along the length of the tube.

23. A probe as defined in claim 22, wherein:
the auxiliary surgical instrument establishes longitudinal seals with the interior surface of the tube along the longitudinal contact position and along the curved support surface; and the passageway is defined by the interior surface of the tube and the exterior surface of the auxiliary surgical instrument between the longitudinal seals.

24. A probe as defined in claim 23, wherein:
the passageway extends on both transverse sides of the auxiliary surgical instrument.

25. A probe as defined in claim 24, further comprising:
sealing means located within the interior of the handle and adapted for contacting the auxiliary surgical instrument and for confining fluid communication within the interior of the handle between the passageway and the fluid flow port.

26. A probe as defined in claim 25, wherein:
the sealing means comprises a resilient elastomer membrane having an opening formed therein through which the auxiliary surgical instrument is inserted and by which a seal is established against the exterior of the auxiliary surgical instrument.

27. A probe as defined in claim 26, further comprising:
pressure relief valve means connected to the handle and operative for releasing pressure communicated through the passageway to the interior of the handle.

28. A probe as defined in claim 27, wherein the handle further includes:
a gas electrosurgical port through which a supply of gas for delivery from the nozzle during gas assisted electro-fulguration is supplied; and
a divider connected within the interior of the handle to divide the interior of the handle into one fluid communication pathway between the gas electrosurgical port and the conduit in the tube and into another separate fluid communication pathway between the fluid flow port and the passageway.

29. A method of performing minimally-invasive, gas-assisted electro-fulguration on a patient using a probe having an elongated tube extending to a distal end of the probe and a handle at a proximal end of the probe, comprising:
inserting a cannula through a body wall of the patient;
expanding the body wall to form a body cavity in which to perform the electro-fulguration;
connecting an assembly of a gas nozzle and an electrode assembly to the tube at the distal end of the probe, the nozzle and electrode assembly having a predetermined configuration to allow the nozzle and electrode assembly to be inserted through the cannula into the body cavity;
inserting the distal end of the probe, the nozzle and electrode assembly and a portion of the tube through the cannula and into the body cavity;
directing the distal end of the probe within the body cavity to a surgical site by manipulating the handle outside of the body cavity and exterior of the body wall;
communicating gas through the tube to the nozzle during gas assisted electro-fulguration;
conducting electrical energy through the tube to the electrode during gas assisted electro-fulguration; and
performing gas assisted electro-fulguration at the surgical site by simultaneously delivering gas and electrical energy from the nozzle and electrode assembly at the distal end of the probe within the body cavity.

30. A method as defined in claim 29 further comprising:
positioning an electrosurgical port on the probe at a position outside of the body cavity and exterior of the body wall;
extending a conduit through the tube from the electrosurgical port to the nozzle and electrode assembly; and
conducting gas and electrical energy through the electrosurgical port to the nozzle and electrode assembly.

31. A method as defined in claim 30 further comprising:
extending a passageway along the tube to the distal end of the tube, the passageway being separate from the conduit and the nozzle; and
communicating fluid with the surgical site at the distal end of the probe by applying at least one of evacuation, irrigation or aspiration through the passageway.

32. A method as defined in claim 31 further comprising:
positioning a fluid flow port on the probe at a position outside of the body cavity and exterior of the body wall;
conducting the fluid flow for the evacuation, irrigation or aspiration through the fluid flow port to the end of the passageway at the distal end of the probe;
dividing an interior of the handle into a first fluid communication pathway and a second fluid communication pathway, the first fluid communication pathway extending between the electrosurgical port and the conduit in the tube, and the second fluid communication pathway extending between the fluid flow port and the passageway; and
separating the first and second fluid communication pathways from one another.

33. A method as defined in claim 31 for use in performing an auxiliary surgical procedure at the surgical site in addition to gas assisted electro-fulguration, further comprising:
extending the passageway longitudinally through the probe from the distal end of the tube into the handle;
positioning an elongated auxiliary surgical instrument in the passageway to extend a portion thereof from the distal end of the tube, the size of the passageway permitting the flow of fluid beside the auxiliary surgical instrument positioned in the passageway; and
performing the auxiliary surgical procedure by using the auxiliary surgical instrument while positioned in the passageway.

34. A method as defined in claim 29 for use in performing an auxiliary surgical procedure at the surgical site in addition to gas assisted electro-fulguration, further comprising:
extending a channel longitudinally through the probe from the distal end of the tube into the handle;
positioning an elongated auxiliary surgical instrument in the channel to extend a portion thereof from the distal end of the tube; and
performing the auxiliary surgical procedure by using the auxiliary surgical instrument while positioned in the channel.

35. A method as defined in claim 34 further comprising:

supporting the auxiliary surgical instrument in the channel to be moved longitudinally along the tube and relative to the distal end of the probe.

36. A method as defined in claim 34 further comprising:

using an auxiliary surgical instrument selected from a group consisting of a standard electrosurgical electrode, a laser fiber optic conduit, an aqua dissection conduit, and a mechanical tool.

37. A method as defined in claim 34 further comprising:

replacing the auxiliary surgical instrument with another auxiliary surgical instrument from the proximal end of the probe while the tube remains inserted through the cannula.

38. A method as defined in claim 29 further comprising:

extending a passageway along the tube from the distal end of the tube to a relief position on the probe outside of the body cavity and exterior of the body wall;

communicating gas pressure within the body cavity through the passageway to the relief position; and relieving excess pressure within the body cavity caused by the delivery of gas during gas assisted electro-fulguration by venting from the relief position the excess gas pressure communicated through the passageway.

* * * * *